US012690822B2

(12) United States Patent
McSweeney et al.

(10) Patent No.: US 12,690,822 B2
(45) Date of Patent: Jul. 28, 2026

(54) ALARM MANAGEMENT FOR MONITORED PHYSIOLOGICAL VARIABLES

(71) Applicant: Welch Allyn, Inc., Skaneateles Falls, NY (US)

(72) Inventors: WonKyung McSweeney, Manlius, NY (US); Allen R. Hart, Maryville, TN (US); Christopher L. Long, Chittenango, NY (US); Rebecca Quilty-Koval, Baldwinsville, NY (US); Chris R. Roberts, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 418 days.

(21) Appl. No.: 18/058,591

(22) Filed: Nov. 23, 2022

(65) Prior Publication Data

US 2023/0165540 A1     Jun. 1, 2023

Related U.S. Application Data

(60) Provisional application No. 63/264,735, filed on Dec. 1, 2021.

(51) Int. Cl.
*A61B 5/00*          (2006.01)
*A61B 5/08*          (2006.01)

(52) U.S. Cl.
CPC ............ *A61B 5/746* (2013.01); *A61B 5/0816* (2013.01); *A61B 5/6822* (2013.01); *A61B 5/7267* (2013.01); *A61B 2562/0219* (2013.01)

(58) Field of Classification Search
CPC ..... A61B 5/746; A61B 5/0816; A61B 5/6822; A61B 5/7267
See application file for complete search history.

(56) References Cited

U.S. PATENT DOCUMENTS

| 5,662,106 | A | 9/1997 | Swedlow et al. |
| 7,267,652 | B2 | 9/2007 | Coyle et al. |
| 7,289,857 | B2 | 10/2007 | Nauck et al. |
| 8,620,591 | B2 | 12/2013 | Wegerich |

(Continued)

FOREIGN PATENT DOCUMENTS

| CN | 102488512 B | 7/2014 |
| CN | 105310685 A | 2/2016 |

(Continued)

OTHER PUBLICATIONS

Baxter. Welch Allyn Connex Spot Monitor: Instructions for Use. Software Version 1.5X. Sep. 2025. (Prior art as Dec. 1, 2021).

*Primary Examiner* — Amanda L Steinberg
*Assistant Examiner* — Laura Hodge
(74) *Attorney, Agent, or Firm* — Merchant & Gould P.C.

(57)          ABSTRACT
A device for monitoring a patient determines a set of predicted physiological variables using a model trained from physiological variables collected from the patient. The device receives a set of measured physiological variables and a motion measurement. The device compares the set of measured physiological variables to the set of predicted physiological variables to determine a residual vector. The device classifies the residual vector using a vector motion error based on the motion measurement, and performs an action based on the classification of the residual vector.

19 Claims, 9 Drawing Sheets

(56) References Cited

U.S. PATENT DOCUMENTS

| | | | |
|---|---|---|---|
| 9,113,778 | B2 | 8/2015 | McNair |
| 9,236,046 | B2 | 1/2016 | Watson et al. |
| 9,265,429 | B2 | 2/2016 | St. Pierre et al. |
| 9,901,261 | B2 | 2/2018 | McCombie et al. |
| 10,413,254 | B2 | 9/2019 | Sarkela et al. |
| 10,456,089 | B2 | 10/2019 | Gourmelon et al. |
| 10,490,049 | B2 | 11/2019 | Ravishankar et al. |
| 10,555,676 | B2 | 2/2020 | McCombie et al. |
| 10,582,858 | B2 | 3/2020 | Volpe et al. |
| 10,595,747 | B2 | 3/2020 | Al-Ali et al. |
| 10,722,179 | B2 | 7/2020 | Pipke |
| 11,004,322 | B2 | 5/2021 | Pekarske |
| 2010/0324377 | A1* | 12/2010 | Woehrle ................. A61B 5/746 |
| | | | 600/300 |
| 2012/0029300 | A1 | 2/2012 | Paquet |
| 2014/0276165 | A1 | 9/2014 | Addison et al. |
| 2017/0281054 | A1* | 10/2017 | Stever ................... G16H 50/20 |
| 2018/0001174 | A1* | 1/2018 | Aoshima .............. A61B 5/1123 |
| 2018/0220900 | A1 | 8/2018 | Meng et al. |
| 2019/0142343 | A1 | 5/2019 | Emmons et al. |
| 2019/0167176 | A1 | 6/2019 | Annoni et al. |
| 2019/0282160 | A1 | 9/2019 | Gilmartin et al. |
| 2020/0029911 | A1 | 1/2020 | Chakravarthy et al. |
| 2020/0038587 | A1 | 2/2020 | Hahn et al. |
| 2020/0054278 | A1* | 2/2020 | Joseph ................... A61B 7/003 |
| 2020/0121254 | A1 | 4/2020 | Mukhopadhyay et al. |
| 2020/0367762 | A1 | 11/2020 | Wallace |
| 2021/0068691 | A1 | 3/2021 | Wang et al. |
| 2021/0085190 | A1 | 3/2021 | Liu et al. |
| 2021/0146082 | A1 | 5/2021 | Härmä et al. |
| 2023/0270389 | A1* | 8/2023 | Randall ................ A61B 5/0022 |
| | | | 600/586 |

FOREIGN PATENT DOCUMENTS

| | | | | |
|---|---|---|---|---|
| CN | 110811595 A | 2/2020 | | |
| CN | 113925482 A * | 1/2022 | ......... | A61B 5/02416 |
| EP | 3 581 093 A1 | 12/2019 | | |
| JP | 6700065 B2 | 5/2020 | | |
| KR | 10-2020-0040669 A | 4/2020 | | |
| WO | 2013/113111 A1 | 8/2013 | | |
| WO | 2014/125402 A1 | 8/2014 | | |
| WO | 2015/164879 A1 | 10/2015 | | |
| WO | 2020/258251 A1 | 12/2020 | | |

* cited by examiner

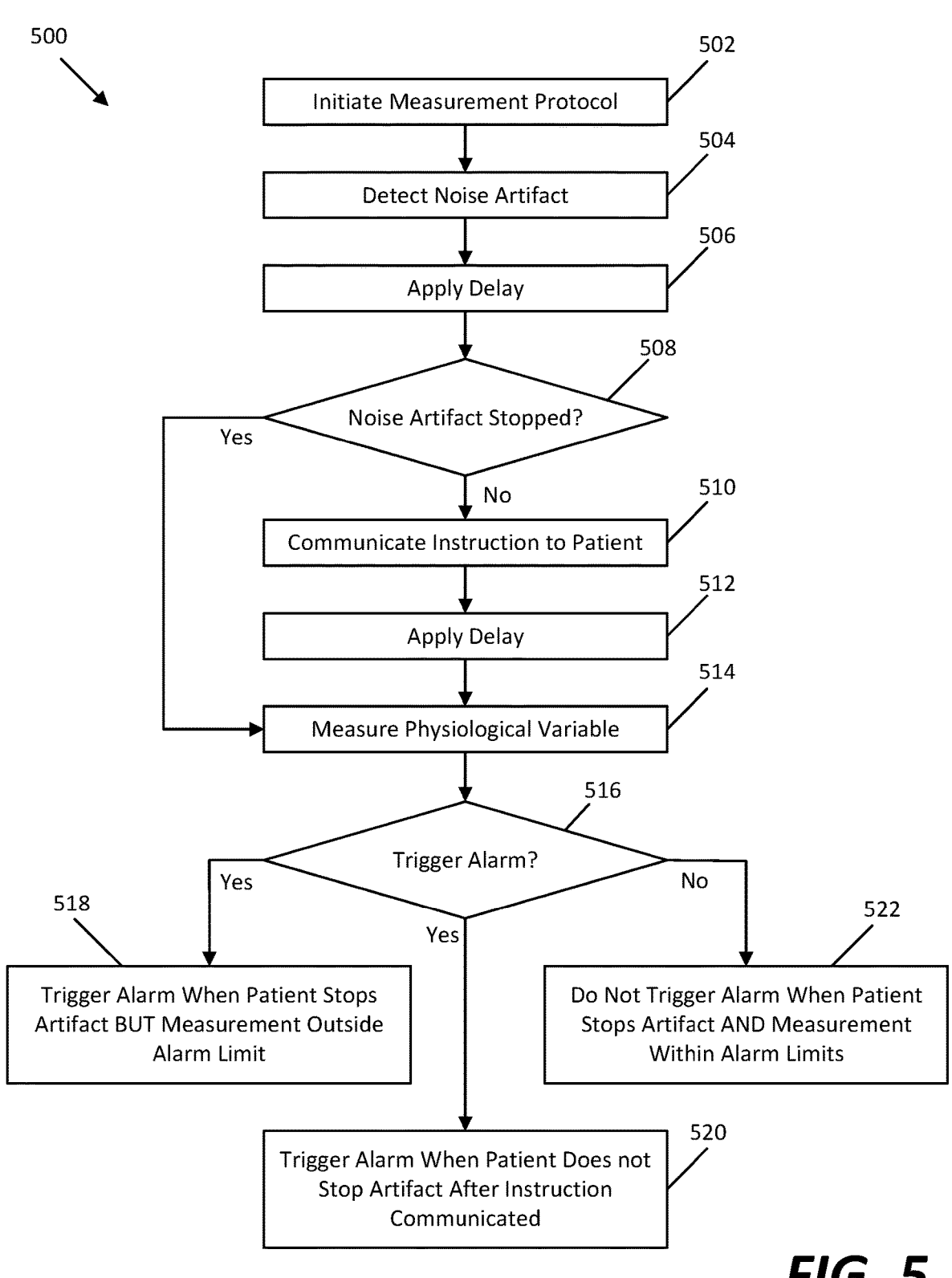

500

502
Initiate Measurement Protocol

504
Detect Noise Artifact

506
Apply Delay

508
Noise Artifact Stopped?

Yes

No

510
Communicate Instruction to Patient

512
Apply Delay

514
Measure Physiological Variable

516
Trigger Alarm?

Yes          No

Yes

518
Trigger Alarm When Patient Stops Artifact BUT Measurement Outside Alarm Limit 522
Do Not Trigger Alarm When Patient Stops Artifact AND Measurement Within Alarm Limits 520
Trigger Alarm When Patient Does not Stop Artifact After Instruction Communicated

Monitor Physiological Variables

704

Train Model

706

Perform Motion Profile

708

Learn Vector Motion Errors

710

Store Model and Vector Motion Errors

800

Lay on Bed Supine  802

Sit Upright  804

Roll from Left to Right Side of Bed  806

Roll from Right to Left Side of Bed  808

Move Arms  810

Cough  812

Talk  814

Eat  816

900

902
Monitor Patient

904
Predict Physiological
Variables
$P_t = M_v(V_{t-x}, V_{t-1})$

906
Receive Measured
Physiological Variables,
Motion Measurement
$V_t, M_t$

908
Determine Residual Vector

910
Classify Residual Vector

912
Perform Action

ALARM MANAGEMENT FOR MONITORED PHYSIOLOGICAL VARIABLES

BACKGROUND

During continuous patient monitoring, an alarm is often set with a pair of upper and lower alarm limits. The alarm is triggered when a patient's monitored vital signs are below the lower alarm limit, or when the patient's vital signs are above the upper alarm limit.

Clinicians are often unable to determine whether an alarm is triggered due to patient deterioration, or due to administered medications, treatments, and noise artifacts. This can lead to confusion regarding the need to respond to the alarm and alarm fatigue.

SUMMARY

In general terms, the present disclosure relates to alarm management for monitoring physiological variables. In one possible configuration, alarm algorithms are installed on a monitor device to predict a patient condition before physiological variable measurements go outside of a traditional threshold range, while mitigating false alarms and alarm fatigue.

In one aspect, a device for monitoring a patient comprises: at least one processing device; and a memory device storing instructions which, when executed by the at least one processing device, cause the device to: determine a set of predicted physiological variables using a model trained from physiological variables collected from the patient; receive a set of measured physiological variables and a motion measurement; compare the set of measured physiological variables to the set of predicted physiological variables to determine a residual vector; classify the residual vector using a vector motion error based on the motion measurement; and perform an action based on the classification of the residual vector.

Another aspect relates to a non-transitory computer readable storage medium storing instructions, which when executed by at least one processing device, cause the at least one processing device to: determine a set of predicted physiological variables using a model trained from physiological variables collected from the patient; receive a set of measured physiological variables and a motion measurement; compare the set of measured physiological variables to the set of predicted physiological variables to determine a residual vector; classify the residual vector using a vector motion error based on the motion measurement; and perform an action based on the classification of the residual vector.

In another aspect, a device for monitoring a patient comprises: at least one processing device; and a memory device storing instructions which, when executed by the at least one processing device, cause the device to: monitor a respiration rate of the patient; determine whether the respiration rate is outside of a threshold range; when the respiration rate is outside of the threshold range, receive data detected from a sensor in an area where the patient is located; process the data to determine whether the patient is talking; and suppress an alarm when it is determined that the patient is talking.

Another aspect relates to a non-transitory computer readable storage medium storing instructions, which when executed by at least one processing device, cause the at least one processing device to: monitor a respiration rate of the patient; determine whether the respiration rate is outside of a threshold range; when the respiration rate is outside of the threshold range, receive data detected from a sensor in an area where the patient is located; process the data to determine whether the patient is talking; and suppress an alarm when it is determined that the patient is talking.

In another aspect, a device for monitoring a patient comprises: at least one processing device; and a memory device storing instructions which, when executed by the at least one processing device, cause the device to: initiate a measurement protocol for measuring physiological variables; apply a first delay after a noise artifact is detected; when the noise artifact does not stop after the first delay, communicate an instruction to the patient to stop an activity relevant to the noise artifact; measure the physiological variables after a second delay; and perform an action based on whether the patient stops the activity and the measure of the physiological variables is within a threshold range.

Another aspect relates to a non-transitory computer readable storage medium storing instructions, which when executed by at least one processing device, cause the at least one processing device to: initiate a measurement protocol for measuring physiological variables; apply a first delay after a noise artifact is detected; when the noise artifact does not stop after the first delay, communicate an instruction to the patient to stop an activity relevant to the noise artifact; measure the physiological variables after a second delay; and perform an action based on whether the patient stops the activity and the measure of the physiological variables is within a threshold range.

Another aspect relates to a method for monitoring a patient, comprising: determining a set of predicted physiological variables using a model trained from physiological variables collected from the patient; receiving a set of measured physiological variables and a motion measurement; comparing the set of measured physiological variables to the set of predicted physiological variables to determine a residual vector; classifying the residual vector using a vector motion error based on the motion measurement; and performing an action based on the classification of the residual vector.

Another aspect relates to a method for monitoring a respiration rate of a patient, comprising: determining whether the respiration rate is outside of a threshold range; receiving data detected from a sensor in an area where the patient is located when the respiration rate is outside of the threshold range; processing the data to determine whether the patient is talking; and suppressing an alarm when it is determined that the patient is talking.

Another aspect relates to a method for monitoring a patient, comprising: initiating a measurement protocol for measuring physiological variables; applying a first delay after a noise artifact is detected; communicating an instruction to a patient to stop an activity relevant to the noise artifact when the noise artifact does not stop after the first delay; measuring the physiological variables after a second delay; and performing an action based on whether the patient stops the activity and the measure of the physiological variables is within a threshold range.

DESCRIPTION OF THE FIGURES

The following drawing figures, which form a part of this application, are illustrative of the described technology and are not meant to limit the scope of the disclosure in any manner.

FIG. 5 schematically illustrates an example of a method of mitigating false alarms by instructing the patient to stop an activity that can cause a false alarm.

DETAILED DESCRIPTION

Figure 1:
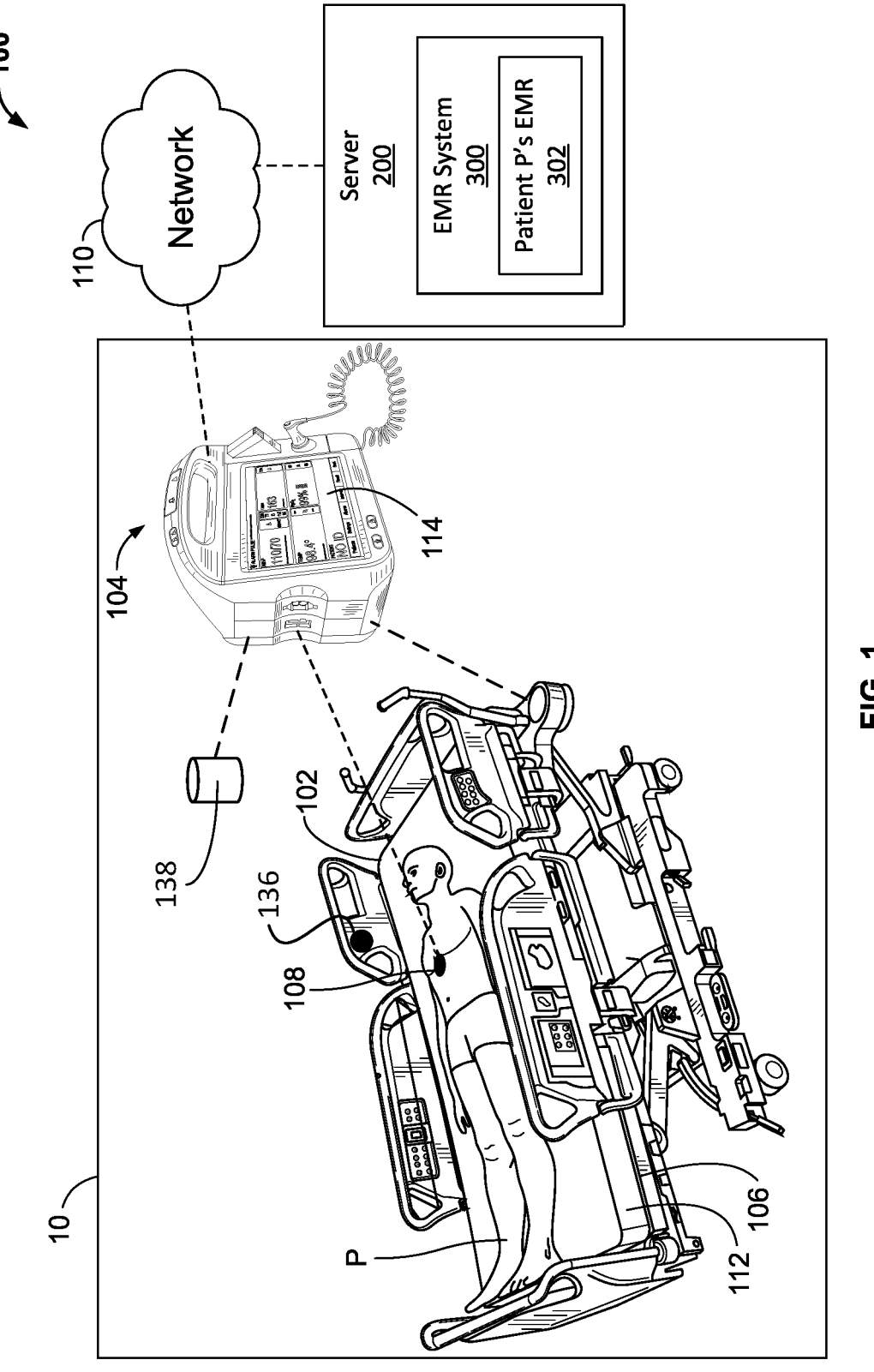
FIG. 1 illustrates an example of a system including a monitor device for monitoring physiological variables of a patient who is shown resting on a patient support system.

FIG. 1 illustrates an example of a system 100 for monitoring physiological variables of a patient P who is shown resting on a patient support system 102. The system 100 includes the patient support system 102, as well as a monitor device 104, a motion sensor 106, and a physiological sensor 108, which are all shown inside an area 10. In some examples, the area 10 is a patient room, a mid-acuity or low-acuity environment, a pre-operative or post-operative holding area, an operating room, a waiting room, or other type of area within a healthcare facility such as a hospital, a surgical center, a nursing home, a long term care facility, or similar type of facility. In further examples, the area 10 can be the patient P's home.

The patient P is a person, such as a patient, who is being clinically treated by one or more clinicians in the area 10. Examples of clinicians include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services.

In the example shown in FIG. 1, the patient support system 102 is a hospital bed. In other examples, the patient support system 102 is another type of bed, lift, chair, wheelchair, stretcher, surgical table, and the like, which can support the patient P in the area 10.

As shown in FIG. 1, the patient support system 102 is communicatively connected to the monitor device 104 through a wireless or wired link. The patient support system 102 includes a frame that supports a mattress 112, and siderails that are coupled to the frame.

The patient support system 102 can also include a microphone and speaker unit 136. In the example shown in FIG. 1, the microphone and speaker unit 136 is installed on a siderail of the patient support system 102. The microphone and speaker unit 136 can be used to detect audio from the patient P, and can also be used to provide instructions to the patient P.

Additionally, or as an alternative to the microphone and speaker unit 136 installed on the patient support system 102, a microphone and speaker unit 138 can be installed inside the area 10 to detect audio from the patient P, and to provide instructions to the patient P. As shown in FIG. 1, the microphone and speaker unit 138 is separate from the patient support system 102.

The microphone and speaker unit 138 can be mounted to a wall, ceiling, fixture, furniture, or equipment in the area 10 where the patient P is located. For example, the microphone and speaker unit 138 can be placed on a nightstand adjacent to the patient support system 102, mounted to a wall or ceiling where the patient support system 102 is located, or can be mounted to the patient support system 102 itself. The microphone and speaker unit 138 is communicatively connected to the monitor device 104 through a wireless or wired link.

Figure 3:
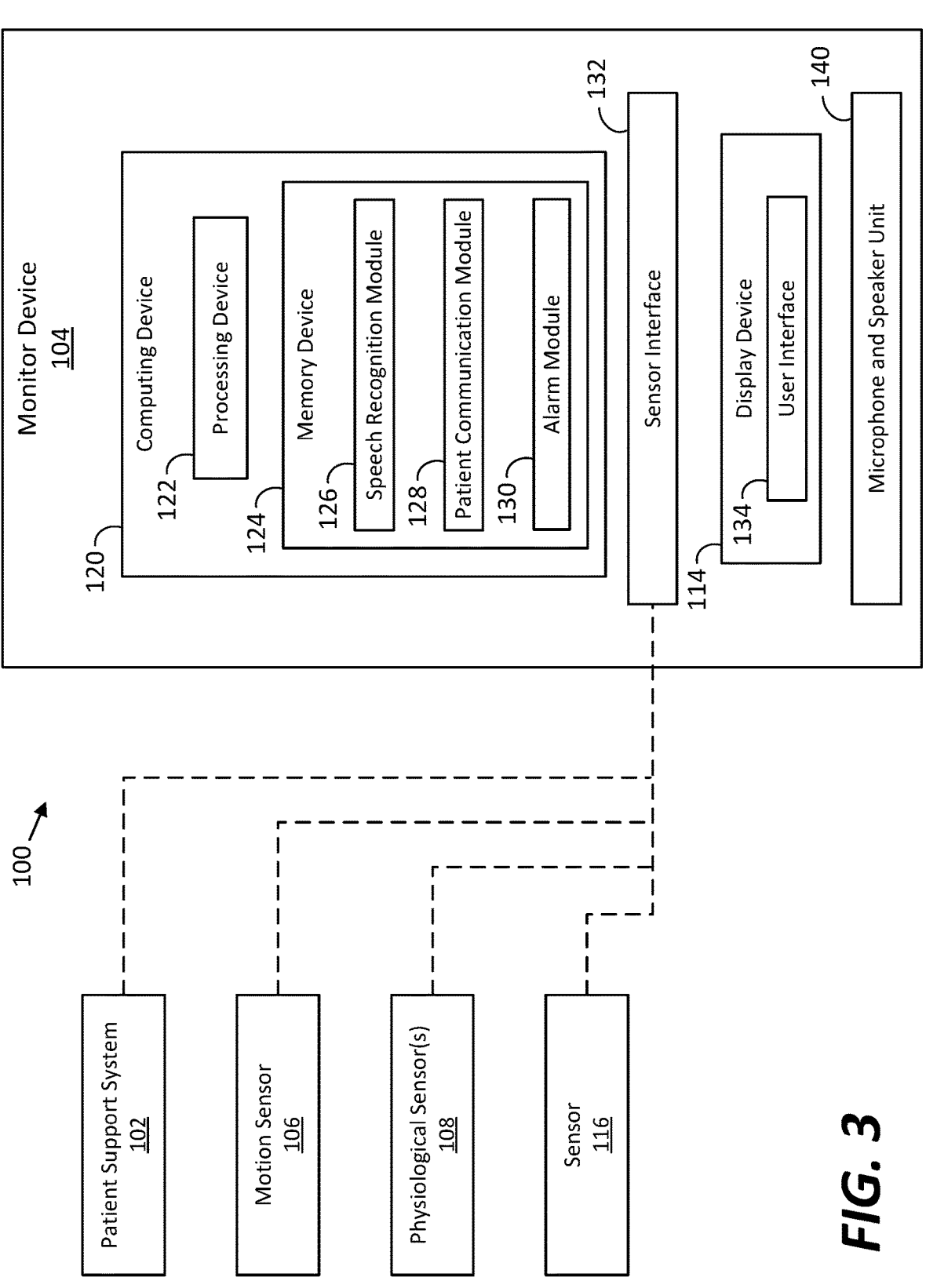
FIG. 3 schematically illustrates an example of the system of FIG. 1, which includes a motion sensor, a physiological sensor, and additional sensor(s) connected to the monitor device.

The monitor device 104 can also be equipped with a microphone and speaker unit 140 (see FIG. 3). When installed on the monitor device 104, the microphone and speaker unit 140 that can be used to detect audio from the patient P, and to provide instructions to the patient P.

The monitor device 104 is an example of an integrator device that receives data from source devices such as the patient support system 102, the motion sensor 106, and the physiological sensor 108. The monitor device 104 includes a computing device 120 (shown in FIG. 3) that processes the data from the sources devices to make decisions such as whether to delay, suppress, or trigger one or more alarms. Additionally, the monitor device 104 includes a display device 114 for displaying the data acquired from the source devices including the patient support system 102, the motion sensor 106, and the physiological sensor 108.

The monitor device 104 may be any suitable type of monitoring device. In the example provided in FIG. 1, the monitor device 104 is illustrated as a multi-parameter device which displays on the display device 114 multiple parameters detected from the source devices. In alternative examples, the monitor device 104 can be a single-parameter device. In certain examples, the monitor device 104 is a spot monitor, and may include the features described in U.S. Pat. No. 9,265,429, which is herein incorporated by reference in its entirety.

Examples of the physiological sensor 108 include an electrocardiogram (ECG) sensor, a blood oxygen saturation/pulse oximeter (SpO2) sensor that can also be used to measure perfusion index (PI), a blood pressure sensor for measuring both systolic and diastolic blood pressure, a heart rate sensor, a respiration rate sensor, an end tidal carbon dioxide (etCO2) sensor that can also be used to measure integrated pulmonary index (IPI), and the like. The physiological sensor 108 can also combine two or more sensors in a single sensor device.

As shown in FIG. 1, the monitor device 104 communicates with a server 200 via a communications network 110. The server 200 operates to manage the patient P's medical history and information. The server 200 can be operated by a healthcare service provider, such as a hospital or medical clinic. The monitor device 104 sends physiological data acquired from the source devices to the server 200 via the connection to the communications network 110. In at least some examples, the server 200 is a cloud server or similar type of server.

The server 200 can include an electronic medical record (EMR) system 300 (alternatively termed electronic health record (EHR)). Advantageously, the server 200 can automatically store the physiological data acquired from the monitor device 104 in an electronic medical record 302 or electronic health record of the patient P located in the EMR system 300 via the connection with the monitor device 104 over the communications network 110.

In the example shown in FIG. 1, the motion sensor 106 is a motion sensor positioned below, within, or on top of a mattress 112 of the patient support system 102. The motion sensor 106 can include piezoelectric sensors, load cells, or combinations thereof that detect movements of the patient P while the patient P is supported on the patient support system 102.

In some examples, the motion sensor 106 may be an accelerometer attached to the patient P, or incorporated into the physiological sensor 108 and/or into one or more other sensing devices that are attached to the patient P. In such examples, physiological sensing and motion detection functions are combined in one device. Multiple such devices may be used on the patient P. For example, a combined ECG/motion detection device and/or a combined respiration rate/motion detection device may be used on the patient P at the same time.

The motion sensor 106 detects motion by the patient P, which can affect or influence the heart rate, blood pressure, and respiration rate data sensed by the physiological sensor 108. The motion sensor 106 senses motion by the patient P (for example by using piezoelectric or load cell sensors positioned below, within, or on top of a mattress 112 or accelerometers attached to the patient P), and transmits the sensed motion data to the monitor device 104 while the physiological sensor 108 senses physiological data such as the heart rate, blood pressure, or respiration rate of the patient P, and transmits the physiological data to the monitor device 104.

The communications network 110 communicates data between one or more devices, such as between the monitor device 104 and the server 200. In some examples, the communications network 110 may also be used to communicate data between one or more devices inside the area 10 such as between the patient support system 102, the monitor device 104, the motion sensor 106, the physiological sensor 108, and other source devices.

The communications network 110 can include any type of wired or wireless connections or any combinations thereof. Examples of wireless connections include broadband cellular network connections such as 4G or 5G. In some examples, wireless connections are also accomplished using Wi-Fi, ultra-wideband (UWB), Bluetooth, radio frequency identification (RFID), and similar types of wireless connections.

Figure 2:
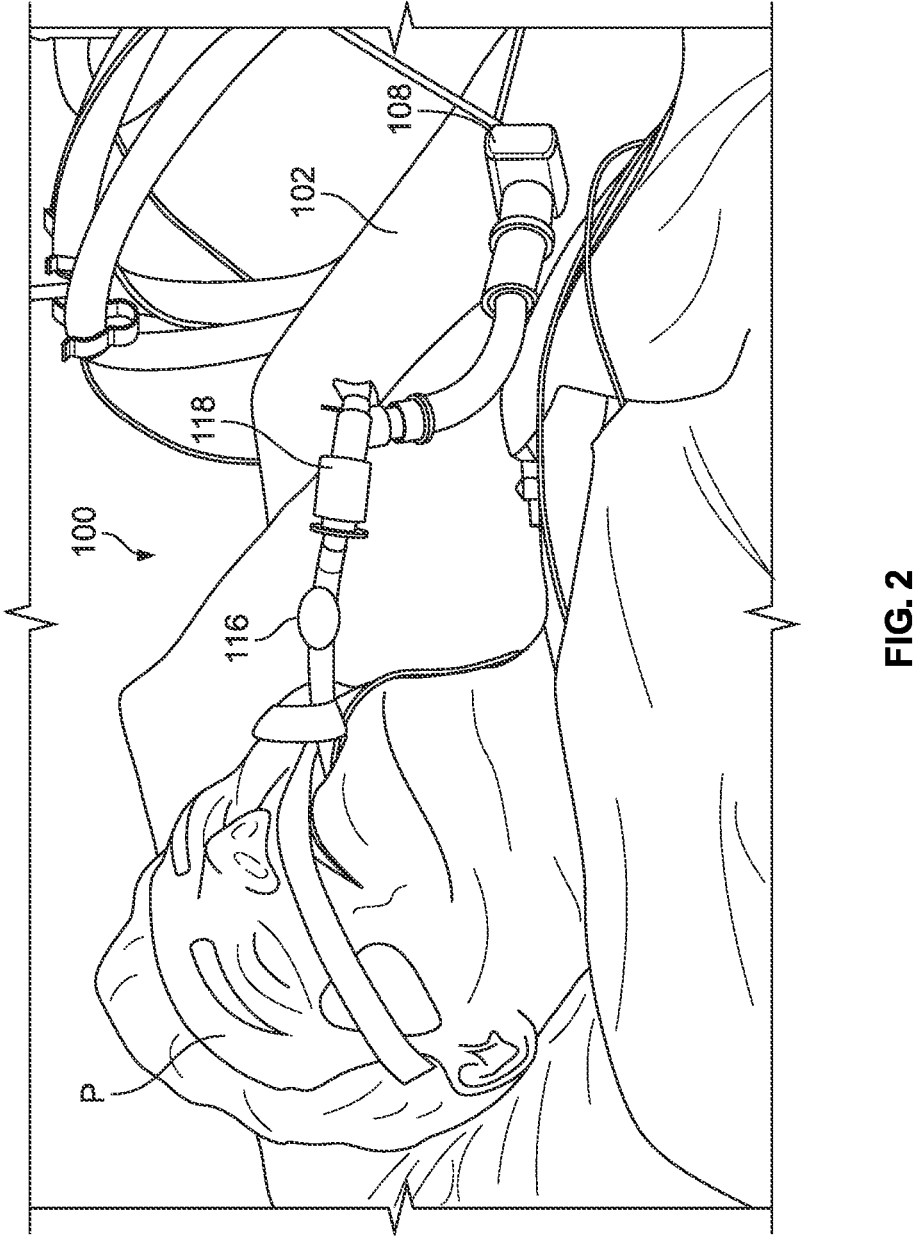
FIG. 2 illustrates an example of a sensor that can be used by the monitor device of FIG. 1, the sensor being shown positioned close to the patient.

FIG. 2 illustrates an example of a sensor 116 that may also be a part of the system 100. As will be described in more detail, the sensor 116 is used to detect when the patient P is talking to suppress false alarms that may result from changes in the respiration rate of the patient P due to the patient P talking. Respiration rate is not reliable when the patient P is talking. Furthermore, when the patient P is comfortably talking and other physiological variables remain stable, false alarms based on potentially erroneous respiration rates can lead to alarm fatigue.

In the example shown in FIG. 2, the sensor 116 is attached to an apparatus 118 connected to the patient P. The apparatus 118 can be a nasal cannula, a tracheal intubation tube, a face mask, a capnography monitor, or similar device attached to the patient P. Alternatively, the sensor 116 can be attached directly to the patient P, or to another object near the patient P.

In some examples, the sensor 116 is a microphone that detects sounds around the patient P. Alternatively, the sensor 116 detects vibrations from where the apparatus 118 is attached to the patient P. For example, the sensor 116 can be positioned proximate the patient's larynx to detect vibrations from the larynx that can be indicative of the patient P talking.

The sensor 116 transmits the detected sounds or vibrations to the monitor device 104. As will be described in more detail with reference to FIG. 3, the monitor device 104 includes a speech recognition module 126 that can distinguish when the patient P is talking such as by identifying words spoken by the patient P, from other sounds and noises made by the patient P, and/or from ambient noise around the patient P inside the area 10.

In the example shown in FIG. 2, the physiological sensor 108 is also attached to the apparatus 118. In this example, the physiological sensor 108 is a capnography sensor that can be used to continuously monitor the respiration rate and etCO2 of the patient P.

In alternative examples, the physiological sensor 108 is a contact-free pad that is placed under the mattress 112 of the patient support system 102, and that measures changes in pressure applied to the pad through the mattress 112, and transmits the measurements to the monitor device 104, which converts the measurements to heart rate, respiration rate, and motion.

As described above, the monitor device 104 processes the sound or vibration data received from the sensor 116 to identify when the patient P is talking. The monitor device 104 can then suppress or delay respiration rate alarms that are triggered when the patient P is talking.

FIG. 3 schematically illustrates an example of the system 100. The monitor device 104 includes a computing device 120 having a processing device 122 and a memory device 124. The processing device 122 is an example of a processing unit such as a central processing unit (CPU). The processing device 122 can include one or more central processing units (CPU). In some examples, the processing device 122 can include one or more digital signal processors, field-programmable gate arrays, or other electronic circuits.

The memory device 124 operates to store data and instructions for execution by the processing device 122, including a speech recognition module 126, a patient communication module 128, and an alarm module 130, which will be described in more detail below. The memory device 124 includes computer-readable media, which may include any media that can be accessed by the monitor device 104. By way of illustrative example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media can include, but is not limited to, random access memory, read only memory, electrically erasable programmable read only memory, flash memory, and other memory technology, including any medium that can be used to store information that can be accessed by the monitor device 104. The computer readable storage media is non-transitory.

Computer readable communication media embodies computer readable instructions, data structures, program modules or other data in a modulated data signal such as a carrier wave or other transport mechanism and includes any information delivery media. The term "modulated data signal"

refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are within the scope of computer readable media.

The monitor device 104 further includes a sensor interface 132 that operates to communicate with the various source devices of the system 100. The sensor interface 132 can include both wired interfaces and wireless interfaces. For example, the patient support system 102, the motion sensor 106, the physiological sensor(s) 108, and the sensor 116 can wirelessly connect to the sensor interface 132 through Wi-Fi, ultra-wideband (UWB), Bluetooth, and similar types of wireless connections. Alternatively, the patient support system 102, the motion sensor 106, the physiological sensor(s) 108, and the sensor 116 can be connected to the monitor device 104 using wired connections that plug into the sensor interface 132.

As shown in FIG. 3, the monitor device 104 includes the display device 114, which operates to display a user interface 134. In some examples, the display device 114 is a touchscreen such that the user interface 134 operates to receive inputs from a clinician. In such examples, the display device 114 operates as both a display device and a user input device. The monitor device 104 can also support physical buttons on a housing of the device that operate to receive inputs from the clinician to control operation of the monitor device and enter data.

Figure 4:
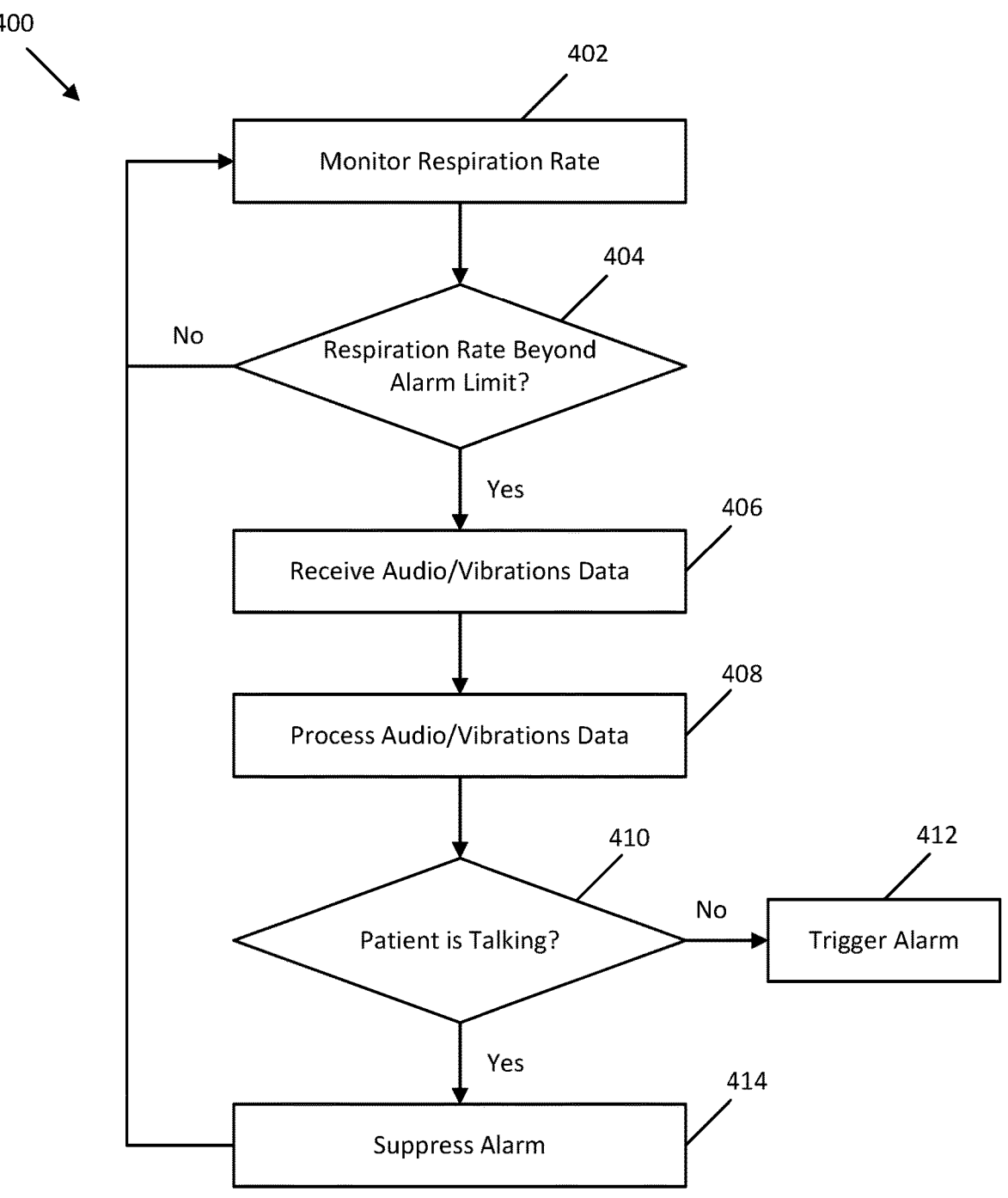
FIG. 4 schematically illustrates an example of a method of mitigating false alarms from a respiration rate sensor.

FIG. 4 schematically illustrates an example of a method 400 of mitigating false alarms from a respiration rate sensor. As an illustrative example, the method 400 can be performed to mitigate false alarms from a capnography sensor (see example of physiological sensor 108 shown in FIG. 2), a contact-free pad positioned under the mattress 112 of the patient support system 102 (see FIG. 1), and/or additional types of sensors that can be used to continuously monitor the respiration rate of the patient P. In certain examples, the method 400 is performed by an integrator device such as the monitor device 104 shown in FIGS. 1-3.

The method 400 includes an operation 402 of continuously monitoring the respiration rate of the patient P. As discussed above, the respiration rate can be continuously monitored by a capnography sensor (see example of physiological sensor 108 shown in FIG. 2), a contact-free pad positioned under the mattress 112 of the patient support system 102 (see FIG. 1), and additional types of sensors that can be used to continuously monitor respiration rate.

Next, the method 400 includes an operation 404 of determining whether the respiration rate of the patient P exceeds an upper alarm limit or is below a lower alarm limit. For example, the respiration rate can exceed an upper alarm limit when the patient P is panting or breathing heavily such as due to shortness of breath, and the respiration rate can be below a lower alarm limit such as due to the patient breathing slowly or not breathing at all.

When the respiration rate of the patient P does not exceed an upper alarm limit and is not below a lower alarm limit (i.e., "No" at operation 404), the method 400 returns to operation 402 and continues to continuously monitor the respiration rate of the patient P.

When the respiration rate of the patient P is determined at operation 404 to exceed an upper alarm limit or to be below a lower alarm limit (i.e., "Yes" at operation 404), the method 400 proceeds to an operation 406 of receiving audio data and/or vibrations data detected from a sensor inside the area 10 that can be used for determining whether the patient P is talking.

In some examples, operation 406 includes receiving audio data and/or vibrations data from the sensor 116 shown in FIG. 2. In further examples, operation 406 includes receiving audio data from the microphone and speaker unit 136 installed on the patient support system 102. In further examples, operation 406 includes receiving audio data from the microphone and speaker unit 138 installed inside the area 10. In yet further examples, operation 406 includes receiving audio data from the microphone and speaker unit 140 of the monitor device 104.

Next, the method 400 includes an operation 408 of processing the audio data and/or vibrations data. Operation 408 can be performed by the speech recognition module 126 installed on the monitor device 104 (see FIG. 3). For example, the speech recognition module 126 can be used to identify and distinguish words that are spoken by the patient P from sounds that may result from the patient P moving, or ambient noise around the patient P. In further examples, the speech recognition module 126 can be used process vibrations received from the sensor 116 to distinguish vibrations that result from the patient P talking (e.g., by movement of the larynx) from vibrations that may result from other movements unrelated to talking.

Next, the method 400 includes an operation 410 of determining whether the patient P is talking. When the patient P is determined to be talking at operation 410 (i.e., "Yes" at operation 410), the method 400 proceeds to an operation 410 of delaying or suppressing a respiration rate alarm because the respiration rate alarm is likely a false alarm. After operation 410, the method 400 returns to operation 402 and continues to continuously monitor the respiration rate of the patient P. When the patient P is not determined to be talking at operation 410 (i.e., "No" at operation 410), the method 400 can proceed to an operation 412 of triggering the respiration rate alarm because the respiration rate alarm is not likely a false alarm.

FIG. 5 schematically illustrates an example of a method 500 of mitigating false alarms by instructing the patient P to stop an activity that can cause a false alarm. The method 500 can be performed in mid-acuity environments where the patient P is able to move around the area 10, such that movements by the patient P can cause motion artifacts that prevent the physiological sensor 108 from accurately measuring one or more physiological variables, resulting in a false alarm. The method 500 allows patient freedom inside the area 10 while minimizing false alarms. The method 500 can be performed by the monitor device 104 when connected to the source devices inside the area 10 such as the patient support system 102, the motion sensor 106, the physiological sensor 108, and the sensor 116.

The method 500 includes an operation 502 of initiating a measurement protocol for one or more physiological variables. The measurement protocol can include an interval mode for measuring the one or more physiological variables. For example, the physiological sensor 108 can be programmed to measure one or more physiological variables at predetermined intervals. As another example, the physiological sensor 108 can be instructed by the monitor device 104 to measure the one or more physiological variables at predetermined intervals. As an illustrative example, the intervals can occur every 15 minutes, 20 minutes, 30 minutes, or every hour.

The one or more physiological variables measured by the measurement protocol can include, without limitation, an electrocardiogram (ECG), blood oxygen saturation, pulse, blood pressure, heart rate, respiration rate, end tidal carbon dioxide (etCO2), perfusion index (PI), integrated pulmonary index (IPI), and the like. Multiple types of physiological variables can be measured by the measurement protocol (e.g., a combination of physiological variables), or a single physiological variable can be measured by the measurement protocol.

Next, the method 500 includes an operation 504 of detecting a noise artifact that can prevent the physiological sensor 108 from accurately measuring the one or more physiological variables during the measurement protocol. For example, the noise artifact can include movement by the patient P detected by the motion sensor 106. Also, the noise artifact can include talking by the patient P detected by the microphone and speaker unit 140 of the monitor device 104 (shown in FIG. 3), by the sensor 116 (shown in FIG. 2), or by the microphone and speaker unit 136 installed on the patient support system 102 (shown in FIG. 1), or by the microphone and speaker unit 138 installed inside the area 10 (shown in FIG. 1).

Next, the method 500 includes an operation 506 of applying a delay for suppressing an alarm when the noise artifact is detected. The delay provides a predetermined amount of time for the noise artifact to naturally stop on its own before triggering the alarm. This can avoid triggering the alarm such as when the noise artifact is due to a temporary event such as the patient P temporarily exiting the patient support system 102 to go use the bathroom.

After the delay terminates, the method 500 proceeds to an operation 508 of determining whether the noise artifact stopped. Operation 508 can include using the motion sensor 106 to determine whether the movement by the patient P has stopped, and/or using the microphone and speaker unit 140 of the monitor device 104, the sensor 116, the microphone and speaker unit 136 installed on the patient support system 102, or the microphone and speaker unit 138 installed inside the area 10 to determine whether the patient P has stopped talking.

When the noise artifact is determined to have stopped (i.e., "Yes" at operation 508), the method 500 proceeds to an operation 514 of measuring the one or more physiological variables in accordance with the measurement protocol. The physiological variables can be measured at operation 514 using any of the physiological sensors described above. For example, operation 514 can include measuring any one or more of an electrocardiogram (ECG), blood oxygen saturation, pulse, blood pressure, heart rate, respiration rate, end tidal carbon dioxide (etCO2), perfusion index (PI), integrated pulmonary index (IPI), and the like.

When the noise artifact is determined not to have stopped (i.e., "No" at operation 508), the method 500 proceeds to an operation 510 of communicating an instruction to the patient P to stop an activity that may be the cause of the noise artifact. The instruction can be an audible instruction that is communicated to the patient P using the microphone and speaker unit 140 of the monitor device 104, the microphone and speaker unit 136 installed on the patient support system 102, or the microphone and speaker unit 138 installed inside the area 10. Also, the instruction can be sent as a notification to a mobile device operated by the patient P such as a smartphone or tablet computer that can vibrate, display the notification identifying the instruction, or generate an audible sound to alert the patient P about the instruction.

In further examples, the instruction can be displayed on the display device 114 of the monitor device 104 which can be positioned next to the patient support system 102 for viewing by the patient P. In further examples, the instruction can be displayed on a television or other type of entertainment device positioned inside the area 10 where the patient P is located.

The instruction can include "stop moving" when the noise artifact includes movement by the patient P detected by the motion sensor 106. The instruction can include stop moving until a beeping noise ends, or until a flashing light stops flashing to allow the patient P to know when they can resume moving around the area 10 without interfering with the measurement protocol.

The instruction can also include "stop talking" when the noise artifact includes talking by the patient P detected by the sensor 116, or by one of the microphone and speaker units 136, 138, 140. Like in the example described above, the instruction can include stop talking until a beeping noise ends, or until a flashing light stops flashing. This allows the patient P to know when they can resume talking without interfering with the measurement protocol.

Next, the method 500 proceeds to an operation 512 of applying a delay after the instruction is delivered to the patient P. The delay provides time for the patient P to stop an activity that may be causing the noise artifact. For example, the delay can provide time for the patient P to return to a rested state such as to sit down or lay down in a supine position.

After the delay in operation 512, the method 500 proceeds to an operation 514 of measuring one or more physiological variables in accordance with the measurement protocol by using the physiological sensors described above. For example, operation 514 can include measuring one or more of an electrocardiogram (ECG), blood oxygen saturation, pulse, blood pressure, heart rate, respiration rate, end tidal carbon dioxide (etCO2), perfusion index (PI), integrated pulmonary index (IPI), and the like.

Next, the method 500 includes an operation 516 of determining whether to trigger an alarm. When the patient stops the activity that was causing the noise artifact and the one or more physiological variables measured at operation 514 are outside of an upper or lower alarm limit, operation 516 proceeds to an operation 518 of triggering an alarm. When the patient does not stop the activity that was causing the noise artifact (or the noise artifact otherwise persists), operation 516 proceeds to an operation 520 of triggering an alarm. When the patient stops the activity that was causing the noise artifact (or the noise artifacts otherwise ceases) and the one or more physiological variables measured at operation 514 are within upper and lower alarm limits, operation 516 proceeds to an operation 522 of not triggering an alarm.

In some examples, operation 522 can also include increasing the delay applied in operation 506 and/or operation 512, and/or the delay for triggering an alarm overall because now there is confidence that the patient P's condition is not worsening, but perhaps is improving due to the patient moving or talking more frequently. By increasing the delay in operation 522, the patient P can move around longer or talk longer before an alarm is triggered. In some examples, the delay is increased to a maximum preset delay or ceiling set by the healthcare facility.

Physiological variables often have causal relationships such that when one physiological variable changes, other physiological variables change as well. This can result from a common cause, such patient motion. For example, an increase in heart rate due to patient motion often causes an increase in respiration rate in order to meet an increased demand for oxygen. Also, patient motion can cause signal noise that leads to erroneous readings.

Figure 6:
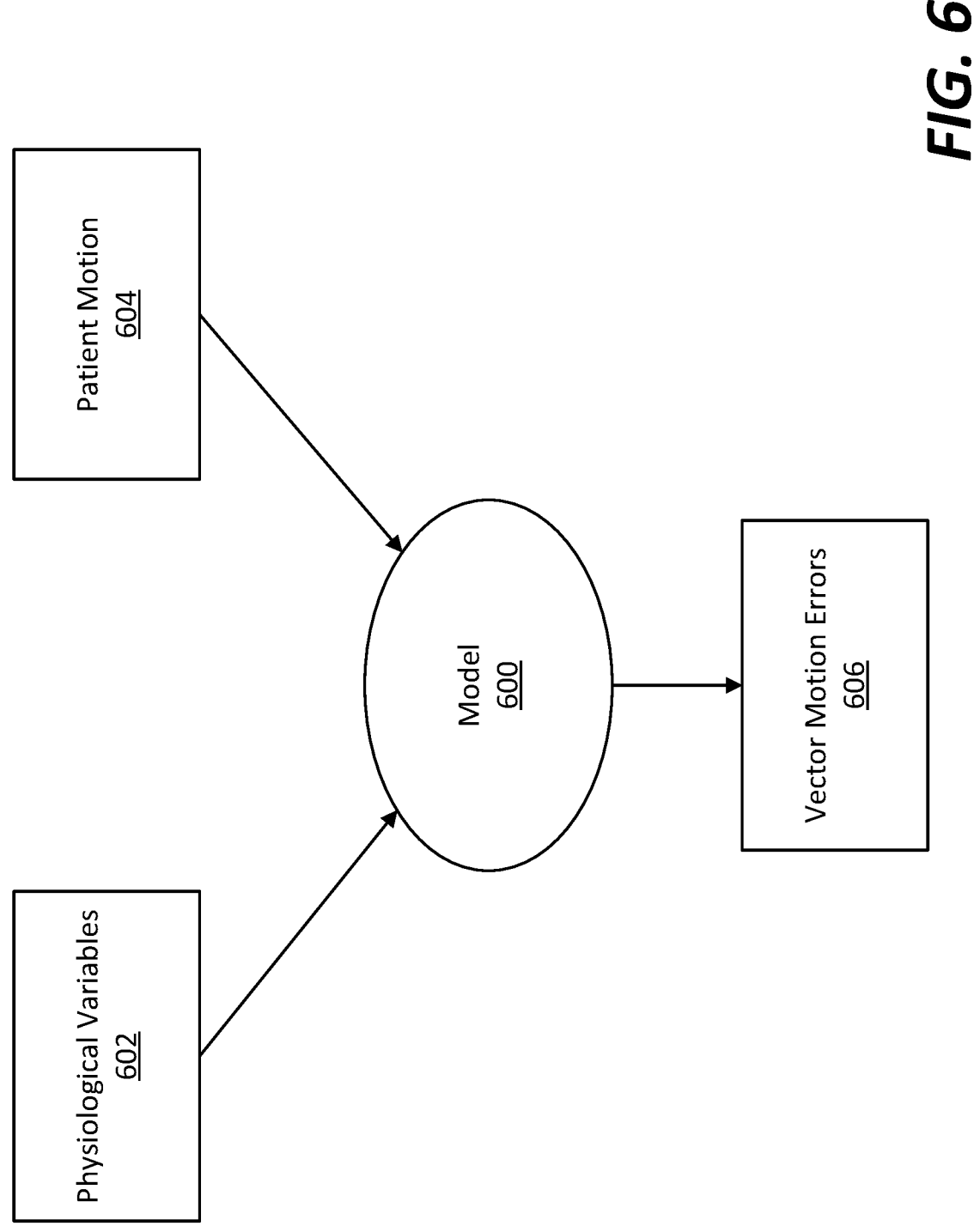
FIG. 6 schematically illustrates an example of a model that can be used by the monitor device of FIG. 1 to detect changes in patient condition.

FIG. 6 schematically illustrates an example of a model 600 that utilizes physiological variables 602 and patient motion 604 to determine vector motion errors 606 that can be used for monitoring the condition of the patient P. The model 600 can be used by the monitor device 104 to make alarm decisions, and to mitigate false alarms and thereby reduce alarm fatigue.

The patient motion 604 influences the physiological variables 602 both individually, and collectively. The model 600 determines the vector motion errors 606 based on collective changes in the physiological variables 602 that can result from the influence of the patient motion 604. Advantageously, the model 600 can be used by the monitor device 104 to detect changes in the condition of the patient P before conventional alarms are triggered, which are typically triggered when an individual physiological variable is outside of an alarm limit.

The model 600 is trained by motion profiling to learn motion driven changes in the physiological variables 602, and to learn motion artifacts that can be caused by the environment in which the physiological sensor 108 is deployed. This can provide the monitor device 104 (when connected to the physiological sensor 108) with integrated sensor sensitivity to patient motion. The training of the model 600 is described in more detail with reference to FIG. 7.

Additionally, the model 600 is personalized for each patient monitored by the monitor device 104. For example, the model 600 can be personalized for the patient P shown in FIGS. 1 and 2, such that the model 600 can be used by the monitor device 104 to more accurately estimate changes in patient P's condition than conventional alarm algorithms.

In some examples, the model 600 is stored locally on the monitor device 104, such as on the memory device 124. In other examples, the model 600 is stored externally, such as on the server 200, and can be accessed by the monitor device 104 via the communications network 110.

Figure 7:
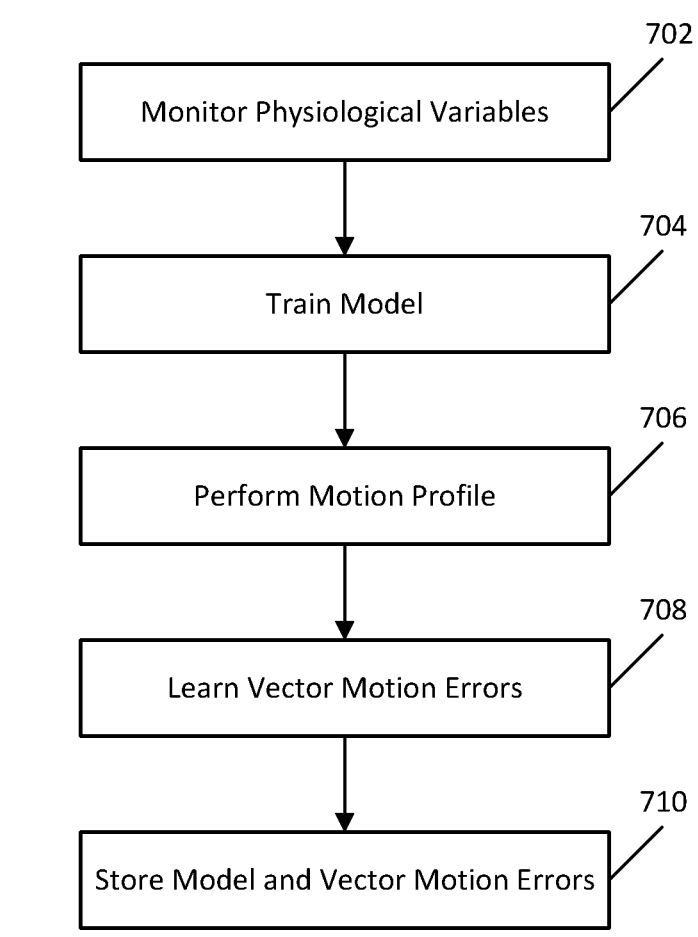
FIG. 7 schematically illustrates an example of a method of building the model of FIG. 6 that can predict changes in patient condition before a traditional alarm is triggered, the model taking into consideration patient motion learned from a patient motion profile.

FIG. 7 schematically illustrates an example of a method 700 of building a model, such as the one shown in FIG. 6. The method 700 provides a way to build a model to factor in the causal relationships across multiple physiological variables over time, and to also factor in patient motion. The method 700 can be performed by the monitor device 104.

As shown in FIG. 7, the method 700 includes an operation 702 of monitoring the physiological variables of the patient P for a predetermined period of time. In some examples, operation 702 occurs when the patient P is admitted to a healthcare facility such as a hospital, a surgical center, a nursing home, a long term care facility, or similar type of facility.

In some examples, the physiological variables are monitored during operation 702 for a predetermined period of time. The physiological variables are collected during operation 702 at a high frequency, such as every second, such that the physiological variables are continuously monitored over the predetermined period of time.

In operation 702, the physiological variables are collected by the monitor device 104 from the physiological sensor 108. Also, the physiological variables are collected in operation 702 while the patient P remains still such that there are no motion artifacts in the data collected form the physiological sensor 108. Examples of the physiological variables that are collected in operation 702 can include, without limitation, heart rate, respiration rate, end tidal carbon dioxide (etCO2), blood oxygen saturation (SpO2), electrocardiogram (ECG), pulse, blood pressure, perfusion index (PI), integrated pulmonary index (IPI), and the like.

Next, the method 700 includes an operation 704 of training a model to determine predicted physiological variables for the patient P based on the physiological variables collected in operation 702. In some examples, operation 704 includes training the model as a multivariate time series model. In some examples, operation 704 includes using vector autoregression for training the model. As described above, the physiological variables are collected in operation 702 while the patient P remains still such that the model is trained in operation 704 without motion artifacts being present in the data used for training the model.

In some examples, certain tests are performed to check the fit of the model. For example, a Durbin-Watson test can be performed to check for residual autocorrelation.

The model is trained in operation 704 to generate sets of predicted physiological variables $P_t$ ($HR_t$, $RR_t$, $etCO2_t$, $SpO2_t$ ... ) with a known error range. The sets of predicted physiological variables are vector outputs. One example is provided in Equation 1 below.

$$P_t = M_v(V_{t-x}, V_{t-1}) \tag{1}$$

In Equation 1, $M_v$ is the model trained from operation 704, and $V_{t-x}$, $V_{t-1}$ are the physiological variables collected over a period of time t-x, t-1.

In certain examples, a set of predicted physiological variables $P_t$ is compared with a set of measured physiological variables $V_t$ ($HR_t$, $RR_t$, $etCO2_t$, $SpO2_t$ ... ) for each time t. The difference between the set of predicted physiological variables $P_t$ and the set of measured physiological variables $V_t$ is a vector that represents a prediction error.

In some examples, the alarm module 130 includes one or more alarms that are based on the prediction error vector. For example, when the prediction error vector exceeds a predetermined threshold, an alarm is triggered. The predetermined threshold can be stored in the memory device 124 of the monitor device 104, and/or can be adjusted by a clinician using the user interface 134 such as to increase or decrease the sensitivity of the alarms.

In further examples, the alarm module 130 can include pre-trained classifiers for classifying the prediction error vectors under various alarm conditions. For example, the pre-trained classifiers can be used to classify the prediction error vectors as high, medium, or low levels of risk for patient deterioration. Advantageously, this information can be utilized by the monitor device 104 to predict an event such as patient deterioration before measurements of an individual physiological variable go outside of a traditional threshold range such as upper and lower alarm limits that are set for the individual physiological variable.

Next, the method 700 includes an operation 706 of instructing the patient P to perform a motion profile that includes a series of patient movements and activities. Operation 706 can be triggered when the patient P is admitted to the healthcare facility, or can be triggered by an event that may indicate that the patient P's condition has changed.

Figure 8:
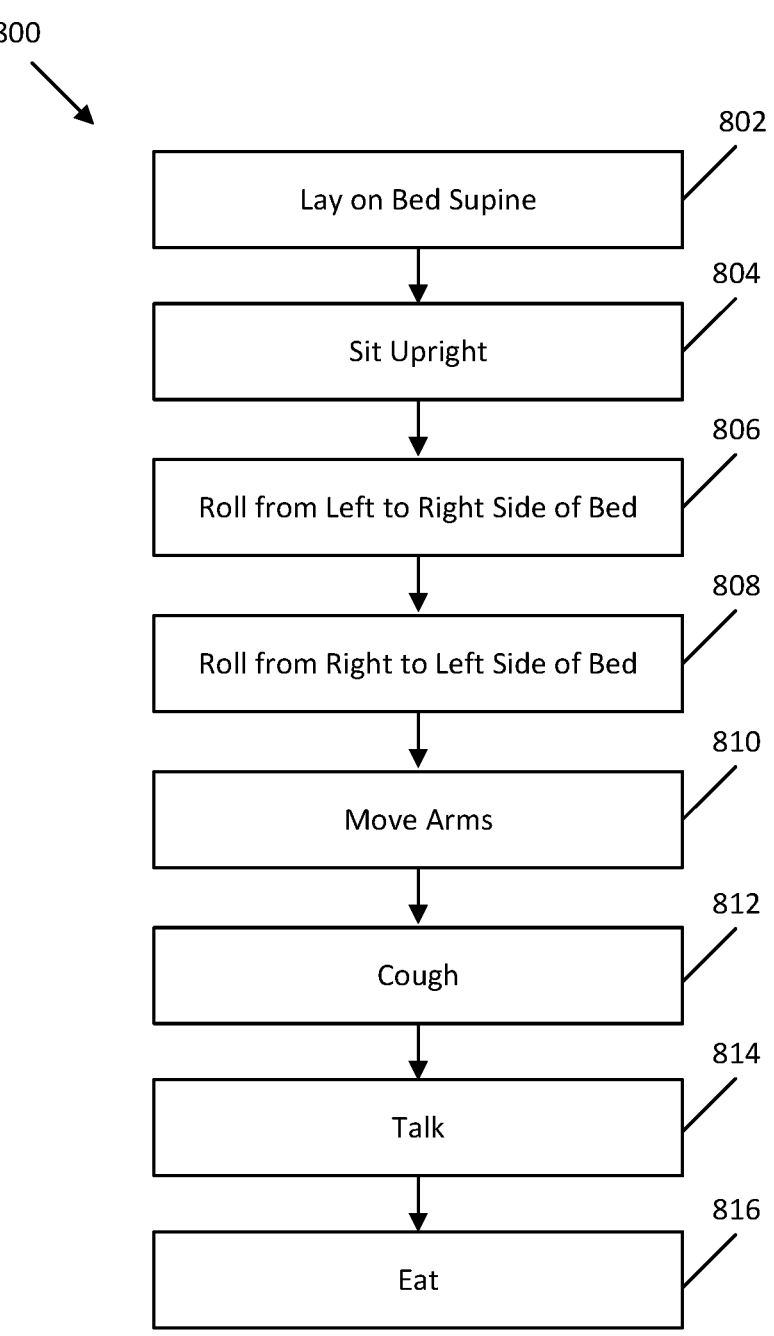
FIG. 8 illustrates an example of a motion profile that can be performed by the patient during an operation of the method of FIG. 7.

FIG. 8 illustrates an example of a motion profile 800 that can be performed by the patient P in operation 706 of the method 700. The motion profile includes patient movements and activities that are expected for the given acuity setting (e.g., mid-acuity or low-acuity environment, a pre-operative or post-operative holding area, an operating room, and the like).

The motion profile 800 can include activities such as, without limitation, a first activity 802 of laying down on bed supine, a second activity 804 of sitting upright, a third activity 806 of rolling from left side of bed to right side of bed, a fourth activity 808 of rolling from right side of bed to left side of bed, a fifth activity 810 of moving arms up and down, a sixth activity 812 of coughing (e.g., coughing repeatedly such as at least every 5 seconds while covering mouth with left or right hand), a seventh activity of talking (e.g., reading text aloud), and an eighth activity of eating (e.g., taking small bites and chewing frequently). Additional activities can include tapping a finger on which a blood oxygen saturation/pulse oximeter (SpO2) sensor is attached, laying on stomach (prone), skootching in bed in any direction when the head of the bed (HOB) is angled at 45 degrees, visually guided breathing, continuously stepping using a step, standing up and sitting down on edge of bed, and the like. Additionally, the motion profile 800 can include transitions between the activities such as a transition between the first activity 802 of laying down on bed supine and the second activity 804 of sitting upright, and so forth.

In some examples, the activities 802-816 are performed sequentially in the order shown in FIG. 8. In other examples, the activities 802-816 are performed in a different order. In further examples, the motion profile 800 can include additional activities, or fewer activities than the ones shown in the example of FIG. 8, which are provided by way of example.

In some examples, the monitor device 104 instructs the patient P to perform the activities 802-816 such as by displaying instructions on the display device 114. Also, or alternatively, the monitor device 104 can instruct the patient P to perform the activities 802-816 by providing audible instructions through use of the microphone and speaker unit 140.

While the motion profile 800 is being performed, operation 706 further includes collecting the measured physiological variables $V_t$ from the physiological sensor 108 while the patient P performs each activity of the motion profile and transitions between the various activities. Also, operation 706 includes collecting motion measurements $M_t$ from the motion sensor 106 while the patient P performs each activity of the motion profile and transitions between the various activities. Activities such as coughing, talking, and/or eating can be recorded by the microphone and speaker unit 140 of the monitor device 104.

Returning back to FIG. 7, the method 700 next includes an operation 708 of training an error model $M_e$ to learn vector motion errors $E_t$ from the motion profile 800 performed in operation 706. For example, the vector motion errors $E_t$ are represented by Equation 2 that follows.

$$E_t = M_e(P_t, V_t, M_t) \qquad (2)$$

where $M_e$ is the error model trained from operation 708, $P_t$ is a set of predicted physiological variables for time t, $V_t$ is a set of measured physiological variables at time t, and $M_t$ is a motion measurement at time t. The vector motion errors $E_r$ can represent a predicted influence that a movement or activity (e.g., rolling in bed, moving arms around, coughing, sitting up, talking, and the like) will have on the physiological variables (e.g., heart rate, respiration rate, end tidal carbon dioxide (etCO2), blood oxygen saturation (SpO2)) of the patient P.

The set of measured physiological variables $V_t$ and the motion measurement $M_t$ that are collected during the motion profile 800 are used to build the error model $M_e$ to learn expected changes (e.g., vector motion errors $E_r$) in the physiological variables based on a type of motion and a level of motion. In some examples, the error model $M_e$ is built using vector autoregression (VAR), long short-term memory (LSTM), and other deep learning techniques.

Thus, the error model $M_e$ learns motion driven changes in the monitored physiological variables of the patient P. The error model $M_e$ can also learn artifacts from the environment in which the physiological sensor 108 is deployed to provide the monitor device 104 with integrated sensor sensitivity to motion.

Once the error model $M_e$ is trained, the error model $M_e$ can also be used by the monitor device 104 to make alarm decisions. For example, the error model $M_e$ can be implemented along with traditional alarm threshold algorithms installed on the monitor device 104 to weigh the severity of any measurement outside of upper and lower alarm limits, and provide a likelihood of the measurement indicating a true event versus a motion triggered transient event. The outputs from the error model $M_e$ can be used by the alarm module 130 to increase a delay duration when a likelihood of the motion triggered transient event is high, and to decrease the delay duration when the likelihood of the motion triggered transient event is low.

Next, the method 700 includes an operation 710 of storing the error model $M_e$ and the vector motion errors $E_t$ that are built and/or learned from operation 708. In some examples, the error model $M_e$ and the vector motion errors $E_t$ are stored locally on the monitor device 104, such as on the memory device 124. In other examples, the error model $M_e$ and the vector motion errors $E_t$ are stored externally, such as on the server 200 or on another external device, and can be accessed by the monitor device 104 such as by using the communications network 110.

Figure 9:
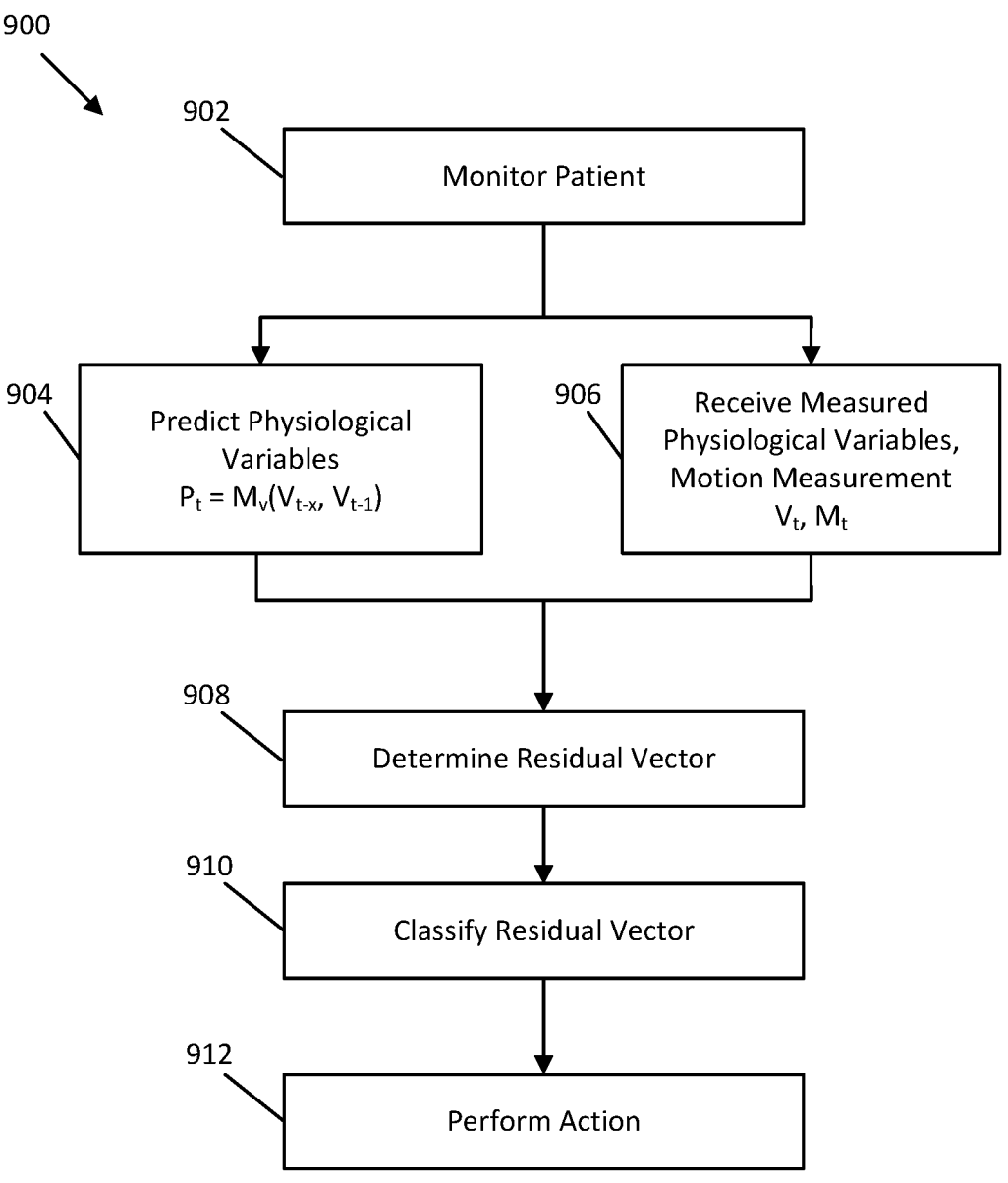
FIG. 9 schematically illustrates an example of a method of using the model built from the method of FIG. 7 to reduce false alarms due to motion artifacts.

FIG. 9 schematically illustrates an example of a method 900 that is performed by the monitor device 104 to detect changes in the condition of the patient P before conventional alarms are triggered, and to also reduce false alarms that can occur due to motion artifacts. The method 900 uses the error model $M_e$ and the vector motion errors $E_t$ determined from the method 700.

As shown in FIG. 9, the method 900 includes an operation 902 of monitoring the patient P. As described above, the patient P can be monitored by using the monitor device 104 as an integrator device that receives data from source devices such as the patient support system 102, the motion sensor 106, the physiological sensor 108, and other devices inside the area 10.

The method 900 includes an operation 904 of determining a set of predicted physiological variables $P_t$ for a time t using the model trained from the method 700. The method 900 further includes an operation 906 of receiving a set of measured physiological variables $V_t$ measured at time t, and a motion measurement $M_t$ measured at time t. As shown in FIG. 9, operations 904, 906 can occur simultaneously, or otherwise substantially at the same time.

Next, the method 900 includes an operation 908 of comparing the set of measured physiological variables $V_t$ received in operation 906 to the set of predicted physiological variables $P_t$ generated in operation 904 to determine a residual vector.

Next, the method 900 includes an operation 910 of classifying the residual vector determined from operation 908 using a vector motion error $E_t$ based on the motion measurement $M_t$. The classification in operation 910 can be a categorical output that indicates a likelihood that the change in the patient P's condition is a true event that is not the result of patient motion. The classification of the residual vector can be used to inform a clinician that the patient's condition may have changed independently of the patient motion, or external factors may have altered the set of measured physiological variables $V_t$ (e.g., motion artifacts and/or signal noise) that are beyond the patient movements and activities expected for the given acuity setting.

Next, the method 900 includes an operation 912 of performing an action based on the classification of the residual vector. The action can include triggering an alarm at operation 912. In some examples, an alarm is triggered on the monitor device 104 as a visual alarm (e.g., flashing light) or an audible alarm (e.g., beeping noise). In further examples, an alarm is sent to a caregiver as a notification for display on a mobile device carried by a caregiver such as a smartphone or tablet computer, or an alarm is sent for display on a nurses' station. In this manner, the method 900 can be performed by the monitor device 104 to detect changes in the condition of the patient P before conventional alarms are triggered.

In some examples, the action can include pausing an alarm. In some further examples, the action can include increasing a delay for triggering an alarm. In further examples, the action can include returning to operation 902 of monitoring the physiological variables of the patient P. In this manner, the method 900 can be performed by the monitor device 104 to mitigate false alarms and thereby reduce alarm fatigue that can result from patient motion.

The various embodiments described above are provided by way of illustration only and should not be construed to be limiting in any way. Various modifications can be made to the embodiments described above without departing from the true spirit and scope of the disclosure.

What is claimed is:

1. A device for monitoring a patient, comprising:
a sensor interface that operates to communicate with a motion sensor positioned on a patient support system and at least one physiological sensor;
a display configured to display data acquired from the at least one physiological sensor;
a speaker;
at least one processing device communicatively connected to the sensor interface, the display, and the speaker; and
a memory device storing instructions which, when executed by the at least one processing device, cause the at least one processing device to:
determine a set of predicted physiological variable values using a model trained using physiological variable measurements collected from the patient;
receive via the sensor interface a set of physiological variable measurements from the at least one physiological sensor and a motion measurement from the motion sensor;
compare the set of physiological variable measurements to the set of predicted physiological variable values to determine a residual vector;
classify the residual vector using a vector motion error based on the motion measurement to indicate a likelihood that a change in a condition of the patient is a true event, wherein the vector motion error represents a predicted influence that the motion measurement has on the physiological variable measurements;
perform an action based on the classification of the residual vector, the action including triggering an alarm on the device by displaying a visual alarm on the display or causing the speaker to output an audible alarm, pausing the alarm, or increasing a delay for triggering the alarm; and
transmit an alarm notification to a remote device when the classification of the residual vector indicates the true event such that the change in the condition of the patient is detected before a conventional alarm is triggered while mitigating false alarms.

2. The device of claim 1, wherein the set of physiological variable measurements includes a heart rate, a respiration rate, an end tidal carbon dioxide, and a blood oxygen saturation.

3. The device of claim 1, wherein the vector motion error is learned from a motion profile that includes a sequence of activities performed by the patient.

4. The device of claim 1, wherein the model is trained without motion artifacts.

5. The device of claim 1, wherein the instructions, when executed by the at least one processing device, further cause the at least one processing device to:
monitor a respiration rate of the patient;
determine whether the respiration rate is outside of a threshold range;
when the respiration rate is outside of the threshold range, collect data detected from a sensor in an area where the patient is located;
process the data to determine whether the patient is talking; and
suppress the alarm when it is determined that the patient is talking.

6. The device of claim 5, wherein the data includes sounds detected from a microphone inside the area where the patient is located.

7. The device of claim 5, wherein the sensor is positioned proximate the patient's larynx, and the data includes vibrations detected from the sensor.

8. The device of claim 1, wherein the instructions, when executed by the at least one processing device, further cause the at least one processing device to:
initiate a measurement protocol for measuring the physiological variable measurements;
apply a first delay after a noise artifact is detected;
when the noise artifact does not stop after the first delay, communicate an instruction to the patient to stop an activity relevant to the noise artifact;
measure the physiological variable measurements after a second delay; and
perform the action based on whether the patient stops the activity and the physiological variable measurements are within one or more threshold ranges.

9. The device of claim 8, wherein the noise artifact is movement by the patient, and the instruction alerts the patient to stop moving.

10. The device of claim 8, wherein the noise artifact is talking by the patient, and the instruction alerts the patient to stop talking.

11. The device of claim 8, wherein the action includes triggering the alarm when the patient does not stop the activity or the physiological variable measurements are measured outside of the one or more threshold ranges after the patient stops the activity.

12. The device of claim 8, wherein the action includes suppressing the alarm when the patient stops the activity and the physiological variable measurements are within the one or more threshold ranges.

13. The device of claim 8, wherein the action includes increasing at least one of the first delay and the second delay.

14. A non-transitory computer readable storage medium storing instructions, which when executed by at least one processing device, cause the at least one processing device to:

determine a set of predicted physiological variable values using a model trained using physiological variable measurements collected from a patient;

receive via a sensor interface a set of physiological variable measurements from at least one physiological sensor and a motion measurement from a motion sensor;

compare the set of physiological variable measurements to the set of predicted physiological variable values to determine a residual vector;

classify the residual vector using a vector motion error based on the motion measurement to indicate a likelihood that a change in a condition of the patient is a true event, wherein the vector motion error represents a predicted influence that the motion measurement has on the physiological variable measurements;

perform an action based on the classification of the residual vector, the action including triggering an alarm by displaying a visual alarm on a display or causing a speaker to output an audible alarm, pausing the alarm, or increasing a delay for triggering the alarm; and transmit an alarm notification to a remote device when the classification of the residual vector indicates the true event such that the change in the condition of the patient is detected before a conventional alarm is triggered while mitigating false alarms.

15. The non-transitory computer readable storage medium of claim 14, further comprising instructions that cause the at least one processing device to:

monitor a respiration rate of the patient;

determine whether the respiration rate is outside of a threshold range;

when the respiration rate is outside of the threshold range, collect data detected from a sensor in an area where the patient is located;

process the data to determine whether the patient is talking; and suppress the alarm when the patient is talking.

16. The non-transitory computer readable storage medium of claim 14, further comprising instructions that cause the at least one processing device to:

initiate a measurement protocol for measuring the physiological variable measurements;

apply a first delay after a noise artifact is detected;

when the noise artifact does not stop after the first delay, communicate an instruction to the patient to stop an activity relevant to the noise artifact;

measure the physiological variable measurements after a second delay; and perform the action based on whether the patient stops the activity and the physiological variable measurements are within a threshold range.

17. A method for monitoring a patient, comprising:

determining a set of predicted physiological variable values using a model trained using physiological variable measurements collected from the patient;

receiving via a sensor interface a set of physiological variable measurements from at least one physiological sensor and a motion measurement from a motion sensor;

comparing the set of physiological variable measurements to the set of predicted physiological variable values to determine a residual vector;

classifying the residual vector using a vector motion error based on the motion measurement to indicate a likelihood that a change in a condition of the patient is a true event, wherein the vector motion error represents a predicted influence that the motion measurement has on the physiological variable measurements;

performing an action based on the classification of the residual vector, the action including triggering an alarm on a monitoring device by displaying a visual alarm on a display or causing a speaker to output an audible alarm, pausing the alarm, or increasing a delay for triggering the alarm; and transmitting an alarm notification to a remote device when the classification of the residual vector indicates the true event such that the change in the condition of the patient is detected before a conventional alarm is triggered while mitigating false alarms.

18. The method of claim 17, further comprising:

monitoring a respiration rate of the patient;

determining whether the respiration rate is outside of a threshold range;

collecting data detected from a sensor in an area where the patient is located when the respiration rate is outside of the threshold range;

processing the data to determine whether the patient is talking; and suppressing the alarm when the patient is talking.

19. The method of claim 17, further comprising:

initiating a measurement protocol for measuring the physiological variable measurements;

applying a first delay after a noise artifact is detected;

communicating an instruction to the patient to stop an activity relevant to the noise artifact when the noise artifact does not stop after the first delay;

measuring the physiological variable measurements after a second delay; and performing the action based on whether the patient stops the activity and the physiological variable measurements are within a threshold range.

* * * * *